United States Patent [19]

Reuter et al.

[11] 4,002,653
[45] Jan. 11, 1977

[54] MANUFACTURE OF ANTHRAQUINONE

[75] Inventors: Peter Reuter, Bad Durkheim; Heinz Eilingsfeld, Frankenthal; Manfred Patsch, Ludwigshafen, all of Germany

[73] Assignee: BASF Aktiengesellschaft, Ludwigshafen (Rhine), Germany

[22] Filed: May 22, 1975

[21] Appl. No.: 579,886

[30] Foreign Application Priority Data

June 26, 1974   Germany ............................ 2430567

[52] U.S. Cl. ................................ 260/369; 252/461
[51] Int. Cl.² .......................................... C09B 1/00
[58] Field of Search ..................... 260/369

[56] References Cited

UNITED STATES PATENTS 3,872,134   3/1975   Wistuba et al. ................. 260/369

*Primary Examiner*—Paul F. Shaver
*Attorney, Agent, or Firm*—Johnston, Keil, Thompson & Shurtleff

[57]         ABSTRACT

Anthraquinone is manufactured by oxidation of diphenylmethane compounds in the gas phase, in the presence of vanadium(V) oxide and titanium dioxide in a specific weight ratio. The anthraquinone which may be manufactured by the process of the invention is a valuable starting material for the manufacture of dyes and pesticides.

14 Claims, No Drawings

MANUFACTURE OF ANTHRAQUINONE

The present invention relates to a process for the manufacture of anthraquinone by oxidation of diphenylmethane compounds in the gas phase in the presence of vanadium(V) oxide and titanium oxide in a specific weight ratio.

U.S. patent application Ser. No. 146,447 relates to a process for the manufacture of anthraquinone by oxidation of diphenylmethane derivatives of the formula

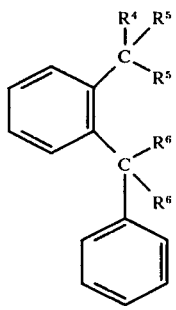

Ia where the individual radicals $R^4$, $R^5$ and $R^6$ are identical or different and each is hydrogen or an aliphatic radical, or the two $R^5$s together and/or the two $R^6$s together are oxo, and/or $R^4$ and one $R^6$ together are an aliphatic radical which is substituted methylene or has at least 2 carbon atoms or, if the $R^5$s together are oxo, may also be unsubstituted methylene, or the two $R^5$s and one $R^6$, or one $R^5$ and the two $R^6$s, or the two $R^5$s and the two $R^6$s can, in each case together, be an aliphatic radical, by means of oxygen in the gas phase in the presence of vanadium(V) compounds as catalysts at elevated temperature.

In all Examples of that Application, vanadium(V) oxide is shown as a component of a vanadium (V) catalyst in which antimony is present as the second metal. Titanium (sic) and certain relative proportions of titanium dioxide and vanadium pentoxide are not mentioned as specific catalysts for diphenylmethane substituted by an aliphatic radical at the 2-position of one ring or for corresponding diphenylmethanes substituted by aliphatic radicals at the methylene group. All the Examples relate to bicyclic compounds which are indene derivatives, indanone derivatives and naphthalene derivatives. The catalysts used are preferably applied to a carrier by a flame spraying or plasma spraying process; these processes give coatings which have no or only a very low internal surface area.

If diphenylmethane substituted by an aliphatic radical at the 2-position of one ring, and corresponding diphenylmethanes substituted by aliphatic radicals at the methylene group are oxidized with the antimony/vanadium(V) catalyst described in the Examples (a reaction not described in the above-mentioned Application), yields of up to 58% of theory are obtained. In addition to anthraquinone, various by-products are obtained. For example, if 2-methyl-diphenylmethane is used as the starting material, the reaction gases generally contain — in addition to anthraquinone — phthalic anhydride, benzoic acid, maleic anhydride, fluorenone, xanthone, benzophenone, benzaldehyde, 3,3'-spirodiphthalide oxygen and concomitant gases, e.g. steam, carbon monoxide and carbon dioxide.

It is true that some of the water-soluble or alkali-soluble by-products can be removed by suitable scrubbing operations. It is known from German Printed Application (DAS) No 1,127,873 that an anthraquinone vapor/air mixture obtained by catalytic oxidation of anthracene vapor over an alkaline vanadium oxide catalyst may be cooled by vaporization of mists of aqueous liquid, whereupon anthraquinone condenses and is obtained as a virtually completely dry powder. This German Printed application teaches that the mist and hence the water introduced are completely and instantly converted to steam in the treatment zone. The temperature of the water introduced is 100° C and hence the carrier gas only loses the amount of heat corresponding to the heat of vaporization of the water. The carrier gas is intended only to cool to a temperature at which the saturation concentration of the vapor-phase contaminants in the carrier gas is not reached. To achieve instant and complete vaporization, certain embodiments regarding atomization of the water and the size of the water droplets are preferred. Distilled or softened water is used to form the mist of liquid. Where carrier gases which contain water vapor are used, e.g. reaction gases from the synthesis of anthraquinone, the vessel in which the treatment is carried out must be well insulated or even heated to prevent condensation of water on the walls of the vessel (cf. column 5, lines 37 to 50).

The said German Printed Application teaches that chilling the sublimate to low temperatures by, for example, a fine spray of water, or by means of cold water, is an uncontrolled process and that neither the particle size nor the purity of the end product condensed in this way can be controlled. As described in column 2 of the German Printed Application, such a process is even less advisable if the sublimed material is accompanied by impurities, as is known to be the case in the manufacture of anthraquinone. It should be emphasized that an impure end product is likely to be obtained.

The main disadvantage of the above process is that the isolation of dry anthraquinone crystals is attended by the risk of dust explosions and fires in the treatment zone (the desublimator) and in the apparatus in which the product is isolated. In addition, if the content of by-products is relatively high, the dew point is correspondingly higher and therefore some of the anthraquinone vapor in the off-gas is lost, whilst the anthraquinone which is condensed may be more heavily contaminated.

However, by-products which are insoluble in water or alkaline solutions, particularly fluorenone, xanthone or benzophenone, cannot be removed by the operations previously mentioned. In subsequent reactions, particularly in the synthesis of dyes, these by-products adversely affect the yield and purity of the products formed, so that additional and uneconomical purification operations are necessary.

It is an object of the present invention to provide a new process whereby anthraquinone may be manufactured more simply and more economically and in greater purity, especially with regard to by-products which are insoluble in water and alkalis.

We have found that the process of U.S. Patent Application Ser. No. 146,447 may be further improved by oxidizing diphenylmethane compounds of the formula

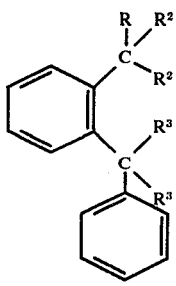

where the individual radicals $R^1$, $R^2$ and $R^3$ may be identical or different and each is hydrogen or an aliphatic radical, in the presence of a catalyst which contains titanium dioxide and vanadium pentoxide in a weight ratio vanadium pentoxide:titanium dioxide of from 0.004:1 to 0.35:1.

If 2-methyl-diphenylmethane is used, the reaction may be represented by the following equation:

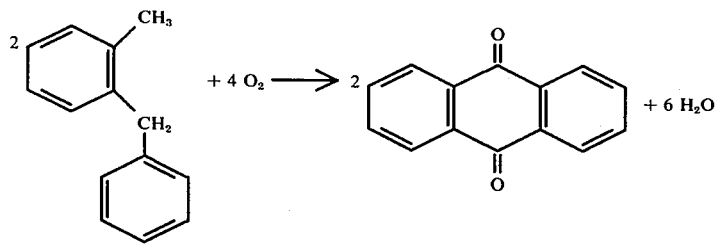

As compared to the state of the art, the process of the invention surprisingly produces anthraquinone more simply and more economically and in greater purity, especially with regard to by-products insoluble in water and alkalis. The oxides of vanadium and titanium, used in the above ratios, prove to be highly selective catalysts for the manufacture of anthraquinone by oxidation of the above diphenylmethane compounds. When they are used, the separation of anthraquinone from the by-products formed during the manufacturing process is greatly simplified, additional purification operations are avoided and hence the economics of dye production are improved. As a rule, only readily volatile and/or readily alkali-soluble by-products are formed in addition to anthraquinone in the process of the invention; for example an alkaline wash of the reaction products condensed out from the reaction gas in general gives anthraquinone which is more than 99.0% pure. All these advantageous results are surprising since it was to be assumed from the state of the art that greater amounts of oxidation products and decomposition products would be formed and in particular that the amounts of insoluble by-products would not be reduced, and the yield of anthraquinone would thus be decreased. Equally, it was not to be expected, in the light of German Published Applicaton (DOS) No. 2,050,798, that this specific catalysis of the oxidation of alkyldiphenylmethanes would be effected by a catalyst which apart from vanadium only contains titanium in a much larger amount and which advantageously has a relatively high internal surface area.

The starting materials I can be manufactured by conventional methods, e.g. 2-benzyltoluene by reaction of benzyl chloride and toluene (Ber., 906 (1873)). The homologs of the above starting materials which are substituted at the methylene group may be obtained analogously, e.g. by reaction of toluene with appropriately substituted styrenes. Preferred starting materials I are those wherein $R^1$, $R^2$ and $R^3$ are identical or different and each is hydrogen or alkyl of 1 to 4 carbon atoms, especially of 1, 2 or 3 carbon atoms. The above radicals may in addition be substituted by groups and/or atoms which are inert under the reaction conditions, e.g. alkoxy groups or alkyl groups, each of 1 to 3 carbon atoms.

The following are examples of suitable starting materials I: 2-butyl-, methoxyethyl-, ethoxymethyl-, 2-isopropyl-, 2-isobutyl-, 2-tert-butyl-, 2-propyl-, 2-ethyl-, 2-sec-butyl-and preferably 2-methyl-diphenylmethane, and the corresponding homologs which are monosubstituted at the methylene group by methoxyethyl, ethoxymethyl, methyl, ethyl, isopropyl, n-butyl, isobutyl or propyl groups, or are disubstituted at the methylene group by two identical or different groups chosen from the above.

As a rule, the oxidation is carried out with excess oxygen. In general, oxygen is employed in the form of air but any mixtures of oxygen and gases which are inert under the reaction conditions, e.g. argon, steam, nitrogen and/or carbon dioxide or flue gas may also be used. Preferably, particularly in the case of 2-methyl-diphenylmethane, from 15 to 700, advantageously from 20 to 164, and especially from 28 to 82, moles of oxygen are employed per mole of starting material I. A suitable amount of starting material I to use is from 20 to 500, advantageously from 100 to 300, grams per liter of catalyst (or of supported catalyst) per hour, in continuous or batchwise operation. The oxides are present in the catalyst in a weight ratio vanadium pentoxide:titanium dioxide of from 0.004:1 to 0.35:1, suitably from 0.01:1 to 0.1:1, preferably from 0.02:1 to 0.059:1, and especially from 0.02:1 to 0.045:1. Compounds which form the oxides of the above metals during manufacture of the catalyst or during the reaction may also be used. Examples of such compounds are hydroxides, oxides of lower valency or salts, e.g. carbonates, bicarbonates or nitrates, of the above metals. Thus, titanium hydroxide, titanium(II) sulfate, titanium(II) oxide, titanium (IV) chloride, titanium(IV) chlorate, titanium carbonate, titanium nitrate, titanium bicarbonate, titanium tartrate, titanium formate, titanium citrate and titanium acetate, and vanadyl oxalate, vanadium formate, vanadium hydroxide, vanadium carbonate, vanadium nitrate, vanadium bicarbonate, vanadium acetate, vanadium tartrate, vanadium chloride, vanadium citrate, ammonium vanadate and vanadium (IV) oxide may be used. The catalyst may contain, in addition to the proportions of titanium dioxide and vanadium pentoxide required by the invention, some proportion of titanium compounds and vanadium compounds which are not essential to the invention, form the above oxides but are as yet unoxidized or only partially oxidized, and of titanium oxides and vanadium oxides of lower valency or of compounds, e.g. titanium vanadate, formed by different reactions of the titanium compound and/or vanadium compound during the reaction according to the invention. The quantities expressed as metal oxide concern solely the titanium dioxide or vanadium(V) oxide present, or formed, during the reaction, and are thus independent of whether, at the beginning of the reaction, the metals are present in the form of another compound or are present, from the start or during the reaction, as titanium dioxide and vanadium pentoxide mixed with such different compounds.

The titanium dioxide may be used in the form of rutile or, preferably, in the form of anatase. It may be used in the anhydrous form or the form of hydrates $TiO_2 . \times H_2O$, e.g. orthotitanic acid or metatitanic acid. The internal surface area of the metal oxides of the catalyst is advantageously from 1 to 80, preferably from 2 to 25, square meters per gram of catalyst. The particle size of the titanium dioxide is advantageously from 0.1 to 1.5, preferably from 0.2 to 0.5, micron.

The catalysts may also be used together with a carrier, e.g. pumice, silicon carbide, silicon oxides, aluminum oxides and, advantageously, steatite. Such supported catatlysts advantageously contain from 1 to 30 per cent by weight of catalyst, based on carrier, the thickness of the catalyst layer on the carrier being from 0.02 to 2 millimeters.

The shape and size of the unsupported catalysts may be varied within wide limits; advantageously, spherical, tabletted or particulate catalysts or extrudates having an average diameter of from 2 to 12 millimeters are used. Unsupported catalysts may be manufactured, for example, by mixing titanium dioxide and vanadium pentoxide, or impregnating titanium dioxide with an aqueous solution of vanadyl oxalate and then drying it, or co-precipitating vanadium pentoxide and titanium dioxide from aqueous solutions of their salts by means of suitable precipitants, e.g. ammonia or alkali metal hydroxides, and drying the product; the catalysts formed can then be converted to appropriate shapes, e.g. by extrusion. The catalysts can also be manufactured by precipitation or evaporation of a solution of ammonium vanadate mixed with appropriate titanium salts, e.g. solutions of titanium(III) oxalate, after which the metal oxide precipitate is filtered off and dried.

If the carrier is added before or during the precipitation, the catalyst is simultaneously finely distributed over the carrier. It is also possible to apply the suspension of the oxides to the carrier by moist oxides with the carrier, to comminute the mixture if necessary and to convert it to appropriate shapes, e.g. by extrusion. Another advantageous method of manufacturing supported catalysts is to add titanium dioxide to a solution of vanadium pentoxide in aqueous oxalic acid or hydrochloric acid and to apply the suspension obtained to the carrier which has been heated, advantageously to from 160° to 500° C and preferably to from 250° to 500° C. In this method, the wettability of the carrier can frequently be improved by adding to the suspension organic water-soluble solvents, such as alkanols, e.g. methanol or ethanol, formamide or dimethylformamide, advantageously in amounts of from 1 to 3.5 percent by weight, based on water.

After drying, the catalyst or supported catalyst can advantageously be calcined in a stream of air, for example at a temperature of from 300° to 700° C. In this connection, reference is made to the information on the manufacture of catalysts given in Houben-Weyl, Methoden der Organischen Chemie, Vol. 4/2, 142–240, and Ullmanns Encyklopadie der technischen Chemie, Vol. 9, 254 et seq. These works also describe methods of applying the catalytic component to inert carriers, not only by impregnation but also, for examply, by spraying or precipitation, followed by calcination of the supported catalyst thus produced.

The oxidation is as a rule carried out at from 200° to 450° C, preferably from 300° to 420° C, under atmospheric or superatmospheric pressure, batchwise or, preferably, continuously. The reaction temperature is measured as the temperature of the salt bath (nitrate melt) by means of which the walls of the tubular reactor are heated, and will hereinafter be referred to as the tube wall temperature. By way of example, starting material I may be oxidized as follows: the diphenylmethane starting compound is vaporized in a stream of air heated to above 150° C. Alternatively, an oxygen-free bleed stream of the reaction off-gases is saturated with the vapor of the starting material and the concentration of starting material I in the reaction mixture is thereby adjusted to the desired value. The gas/vapor mixture is then passed through the catalyst bed in a reactor, at the reaction temperature. Suitable reactors are tubular reactors cooled by means of a salt bath, fluidized-bed reactors with built-in cooling elements, or reactors having a plurality of catalyst beds with intermediate cooling means. The end product is then isolated from the reaction mixture by conventional methods; for example, the gases leaving the reactor are passed through one or more separators. The anthraquinone may then, if necessary, be freed from by-products by washing with water of alkaline solution. The end product can also be isolated by passing the gaseous reaction mixture into water or into an alkaline solution, wereby the anthraquinone is obtained as an insoluble solid of high purity.

The anthraquinone manufactured by the process of the invention is a valuable starting material for the manufacture of dyes and pesticides. Information on its use may be found in the above publications and Ullmanns Encyklopadie der technischen Chemie, Vol. 3, 659 et seq.

Parts, in the Examples, are by weight, and bear the same relation to parts by volume as the kilogram to the liter.

EXAMPLE 1

(a) Manufacture of the catalyst 8.18 parts of vanadyl oxalate (corresponding to 4 parts of $V_2O_5$) are dissolved in 200 parts of water, 96 parts of titanium dioxide and 32 parts of formamide are added and the resulting suspension is applied to steatite spheres 6 mm in diameter which have been heated to 300° C. A coated sphere contains 4 parts of catalyst (vanadium pentoxide and titanium dioxide) and 96 parts of carrier. The catalyst itself consists of 96 percent by weight of titanium dioxide and 4 percent by weight of vanadium pentoxide.

(b) Oxidation 64 parts of the catalyst manufactured according to (a) are introduced into a tubular reactor (25 mm internal diameter). A mixture of 400,000 parts by volume of air and 13.6 parts of 2-methyl-diphenylmethane per hour is passed over the catalyst. The tube wall temperature is 388° C. The gaseous reaction mixture leaving the reactor is cooled to 60° C, which causes the end product to condense. The uncondensed part is washed out with water. The water-insoluble constituents are combined with the condensate. 54.4 parts of 2-methyl-diphenylmethane give 49.9 parts of crude end product containing 86 percent by weight of anthraquinone. After treatment with 1,000 parts of a 10 percent strength by weight sodium carbonate solution, 42.8 parts of anthraquinone of melting point 286° C are obtained; this corresponds to a yield of anthraquinone of 69.2% of theory, based on 2-methyl-diphenylmethane employed. Neither fluorenone nor xanthone are detectable, by UV absorption and gas chromatography, in the end product and in the wash filtrates.

EXAMPLE 2

The reaction is carried out analogously to Example 1 with a catalyst which contains 16 parts of $V_2O_5$ and 84 parts of $TiO_2$. 37.5 parts of anthraquinone of melting point 286° C are obtained, corresponding to 60.6% of theory, based on starting material I employed; the product contains no appreciable amounts of fluorenone and xanthone.

We claim:

1. In a process for the manufacture of anthraquinone by oxidation of diphenylmethane derivatives of the formula

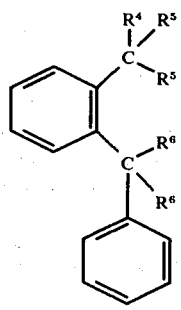

where the individual radicals $R^4$, $R^5$ and $R^6$ are identical or different and each is hydrogen or an aliphatic radical, or the two $R^5$s together and/or the two $R^6$s together are oxo, and/or $R^4$ and one $R^6$ are together an aliphatic radical which is substituted methylene or has at least 2 carbon atoms or, if the $R^5$s and one $R^6$, or one $R^5$ and the two $R^6$s, or the two $R^5$s and the two $R^6$s can, in each case together, be an aliphatic radical, by means of oxygen in the gas phase in the presence of vanadium(V) compounds as catalysts, at elevated temperature, the improvement comprising: oxidizing a diphenylmethane compound of the formula

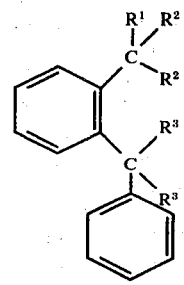

in which the individual radicals $R^1$, $R^2$ and $R^3$ are identical or different and each is hydrogen or an aliphatic radical, in the presence of a catalyst which contains titanium dioxide and vanadium pentoxide in a weight ratio vanadium pentoxide: titanium dioxide of from 0.004:1 to 0.35:1.

2. A process as claimed in claim 1, wherein the oxidation is carried out in the presence of a catalyst which contains titanium dioxide and vanadium pentoxide in a weight radio vanadium pentoxide: titanium dioxide of from 0.01:1 to 0.1:1.

3. A process as claimed in claim 1, wherein the oxidation is carried out in the presence of a catalyst which contains titanium dioxide and vandium pentoxide in a weight ratio vanadium pentoxide: titanium dioxide of from 0.02:1 to 0.059:1.

4. A process as claimed in claim 1 wherein the oxidation is carried out in the presence of a catalyst which contains titanium dioxide and vanadium pentoxide in a weight ratio vanadium pentoxide: titanium dioxide of from 0.02:1 to 0.045:1.

5. A process as claimed in claim 1, wherein the oxidation is carried out with from 20 to 500 grams of starting material I per liter of catalyst.

6. A process as claimed in claim 1, wherein the oxidation is carried out with titanium dioxide in the anatase form.

7. A process as claimed in claim 1, wherein the oxidation is carried out with a catalyst in which the internal surface area of the metal oxides is from 1 to 89 meters per gram of catalyst.

8. A process as claimed in claim 1, wherein the oxidation is carried out with titanium dioxide of particle size from 0.1 to 1.5 microns.

9. A process as claimed in claim 1, wherein the oxidation is carried out with a supported catalyst containing from 1 to 30 percent by weight of catalytically active material, based on carrier, the thickness of the catalytically active layer on the carrier being from 0.02 to 2 millimeters.

10. A process as claimed in claim 1, wherein the oxidation is carried out at from 200° to 450° C.

11. A process as claimed in claim 1, wherein the oxidation is carried out at from 300° to 420° C.

12. The process set forth in claim 1 wherein the diphenylmethane material I, $R^1$, $R^2$ and $R^3$ are identical or different and each is hydrogen or alkyl of 1 to 4 carbon atoms.

13. The process set forth in claim 12 wherein said alkyl group is substituted with additional alkyl group of 1 to 3 carbon atoms.

14. The process set forth in claim 12 wherein said alkyl is substituted with alkoxy of 1 to 3 carbon atoms.

* * * * *

UNITED STATES PATENT AND TRADEMARK OFFICE
CERTIFICATE OF CORRECTION

PATENT NO. : 4,002,653
DATED : January 11, 1977
INVENTOR(S) : REUTER ET AL

It is certified that error appears in the above-identified patent and that said Letters Patent are hereby corrected as shown below:

In the Claims;

Claim 2, line 4, delete "radio" and insert --ratio--.

Claim 7, line 3, delete "89" and substitute --80 square--.

Signed and Sealed this

Twenty-first Day of March 1978

[SEAL]

Attest:

RUTH C. MASON
Attesting Officer

LUTRELLE F. PARKER
Acting Commissioner of Patents and Trademarks